(12) United States Patent
Facchiano et al.

(10) Patent No.: US 6,627,769 B2
(45) Date of Patent: Sep. 30, 2003

(54) RGD-ANALOG NON-PEPTIDIC MOLECULES HAVING ANTI-ADHESIVE, ANTI-MIGRATION AND ANTI-PROLIFERATIVE EFFECTS

(75) Inventors: Antonio Facchiano, Rome (IT); Francesco Facchiano, Rome (IT); Ivan Rossi, Casalecchio di Reno (IT); Rita Casadio, Bologna (IT)

(73) Assignee: Provincia Italiana Della Congregzaione dei Figli Dell'Immacolata Concezione - Istituto Dermopatico Dell'Immacolata, Rome (IT)

( * ) Notice: Subject to any disclaimer, the term of this patent is extended or adjusted under 35 U.S.C. 154(b) by 0 days.

(21) Appl. No.: 10/077,948

(22) Filed: Feb. 20, 2002

(65) Prior Publication Data
US 2002/0119932 A1 Aug. 29, 2002

(30) Foreign Application Priority Data
Feb. 21, 2001 (IT) ..................................... RM2001A0089

(51) Int. Cl.[7] ..................... C07C 229/02; C07C 279/00; A61K 31/195

(52) U.S. Cl. ..................... 562/439; 562/560; 562/440; 548/540; 514/423; 514/563; 514/564; 514/565

(58) Field of Search ................................. 562/560, 439, 562/440; 548/540; 514/563, 564, 565, 423

(56) References Cited

U.S. PATENT DOCUMENTS

| 5,519,005 A | | 5/1996 | Lider et al. | |
|---|---|---|---|---|
| 5,599,984 A | * | 2/1997 | Bianchi et al. | ............. 564/157 |

FOREIGN PATENT DOCUMENTS

| EP | 0 644 181 A1 | 3/1995 |
|---|---|---|
| WO | 92/13552 | 8/1992 |

* cited by examiner

Primary Examiner—Shailendra Kumar
(74) Attorney, Agent, or Firm—Young & Thompson

(57) ABSTRACT

Novel molecules without intramolecular peptidic bonds, able to mimic the RGD peptide, containing ARG-GLY-ASP motif "arginine-glycine-aspartic acid" (that is a potent inhibitor, in vivo and in vitro, of cellular adhesion) In vitro experimentation demonstrated that said molecules are efficient inhibitors of RASMC adhesion, proliferation and migration.

24 Claims, 1 Drawing Sheet

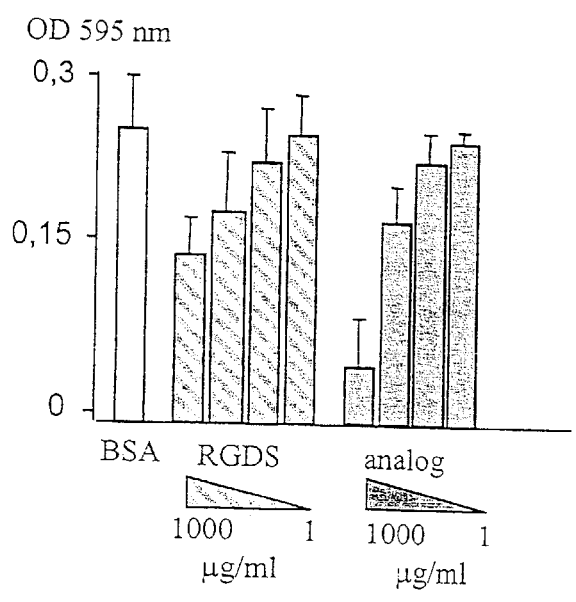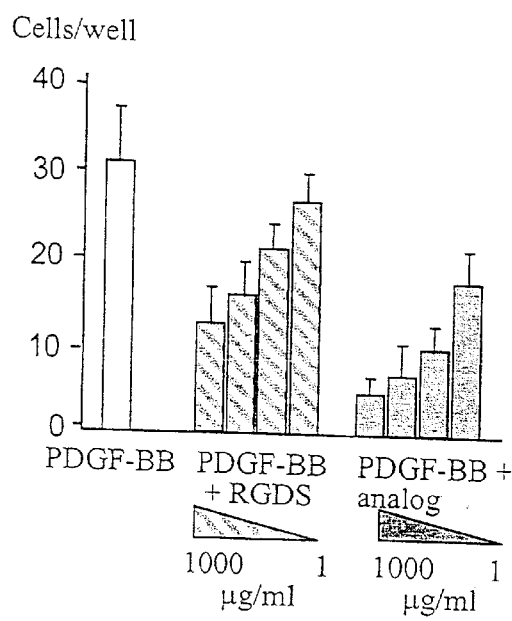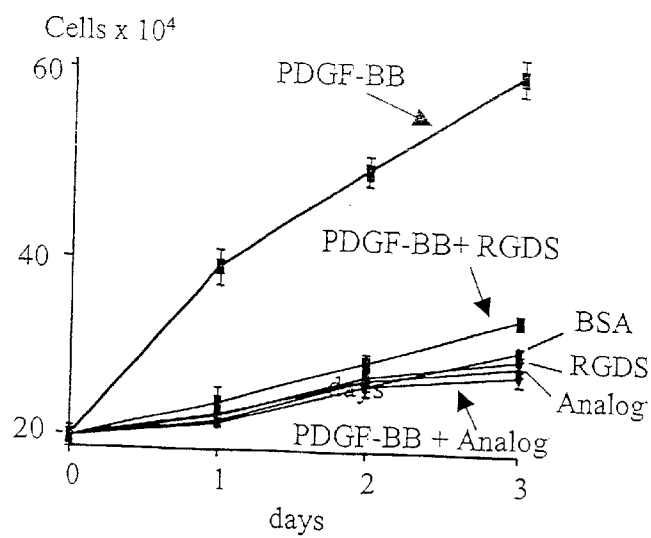

RGD-ANALOG NON-PEPTIDIC MOLECULES HAVING ANTI-ADHESIVE, ANTI-MIGRATION AND ANTI-PROLIFERATIVE EFFECTS

The present invention concerns the identification of new synthetic molecules able to mimic peptides with biological activity, i.e. peptide-like molecules or peptidomimetic molecules. More particularly, the present invention relates to the identification of new molecules with no intramolecular peptidic bonds and able to mimic the RGD motif. In fact, it is known that the RGD motif is a potent inhibitor, in vivo and in vitro, of cellular adhesion.

In vitro experimentation on rat smooth muscle cells (RASMC) demonstrated that these new peptidomimetic molecules are efficient inhibitors of RASMC proliferation and migration (modification of cell migration and proliferation occurs in many vascular diseases such as atherosclerosis and restenosis which have a high social impact) and could be used as inhibitors of tumor cells migration towards potential metastatic sites.

The lack of proper peptide bounds makes said molecules less sensible to in vivo proteolytic degradation. It is well known that proteolytic degradation is a catabolic mechanism which usually reduce or block in vivo biological effects of peptidic molecules having in vitro activity.

Therefore, the peptidomimetic molecules, object of the invention, are potentially more stable and consequently show higher in vivo activity than the corresponding template peptide used for their design.

Vascular diseases represent one of the major cause of morbidity and mortality in western countries. Ischemic diseases are mainly due to atherosclerosis, thrombotic events, and other phenomena such as restenosis after angioplasty. In addition, vascular changes lead to neovascularization during solid tumours growth. For this reason, molecules active in controlling the growth of vascular cells and vessel walls are largely investigated for the potential benefits in a variety of socially relevant diseases.

It has been demonstrated that angiogenesis depends on the adhesion of vascular cells to the extracellular matrix and that the protein so called $\alpha_v\beta_3$ integrin is required for this process (Brooks et al. Science, 1994, 264, 569–571).

Consequently, peptides containing the ARG-GLY-ASP motif "arginine-glycine-aspartic acid" (RGD motif), which are integrin-inhibitors, may exert anti-angiogegenic properties (Friedlander. et al., Science 1995, 270, 1500–1502; Woodard et al., J. Cell Sci. 1998, 1930–1935) and anti-neoplastic activity (Hammes. et al., Nat.Medicine, 1996, 2, 529–533;.Carron. et al. Cancer Res. 1998, 1930–1935) and anti-metastatic activity (Fujii. et al., Oncology Res. 1996, 8, 333–342).

Moreover, it has been shown that RGD-containing proteins and RGD-containing short peptides modulate blood coagulation, cell growth, cell migration and cell adhesion to extracellular matrix (Rouslhti et al., Annu Rev Cell Dev Biol. 1996, 12, 697–715; Ojima et al., Bioorganic & Medecin Chemistry 1997, 3, 337–360; Wang et al., Curr.Med.Chem., 2000, 7, 74–80).

Besides that, RGD-analogs have been shown to induce apoptosis under different experimental conditions (Modlich et al., Lab.Invest. 1996, 74, 771–780; Yeh et al., Blood 1998, 92, 3268–3276; Buckley et al., Nature 1999, 397, 534–539).

Considering these data, RGD-analogs peptides can efficiently induce apoptosis of tumour cells and of actively proliferating vascular cells.

The use of small biologically active peptides is currently under strong investigation, due to the relative cost of synthesis and to the restricted in vivo side effects of these small peptides in comparison with the parent whole proteins. Unfortunately, small peptides are usually unstable molecules; they are degradable by proteases and they can be recognised as non-self by the immune system and thus eliminated rapidly loosing their biological effects. Therefore, according to the present invention, once the active site of specific proteins was identified, the following step consisted in the identification of molecules mimicking said active site, but having different chemical characteristics (i.e. peptides bounds or antigenic activity) in order to reduce their catabolism and consequently increase their activity in vitro as well as in vivo.

Nowadays large investigation is on RGD-containing peptides, because, as already mentioned, they show strong activity in vitro as well in vivo as inhibitors of integrin-mediated diseases.

Non-peptidic analogs of RGD-peptides are designed to obtain molecules which are more stable in vivo, lacking of proteolitic-sites and undergoing a slower catabolic degradation in vivo (Wang et al., Curr.Med.Chem., 2000, 7, 74–80; Horton et al., Exp.Nephrol., 1999, 7, 178–184). Said peptides-like molecules are named peptidomimetics since they mimic the original compound, but the absence of peptidic bonds, avoid their degradation by proteases and consequently they are more stable in vivo.

The use of this novel approach (peptidomimetics) represent a new and spreading field of research, supported by new chemical compounds available on the market. The use of specific software able to detect similar shapes or three-dimensional structures and similar electronic distributions in different molecules allows to identify the building blocks most suitable to be used as alternative to the amino acids for the construction of peptidomimetic molecules.

Object of the present invention is a novel family of synthetic non-peptidic molecules, able to mimic the RGD motif and to inhibit cellular adhesion, migration and proliferation: said family of molecules is at least equally or more active in vitro in comparison to the corresponding template, and potentially more stable in vivo.

According to the present invention, in the first step a peptidic molecule has been chosen as template to design peptidomimetic ore peptide-like molecules in the following steps. For this purpose, RGD-containing peptides ("arginine-glycine-aspartic acid"), involved in several biological functions, as modulation of adhesion between cells and between cells and extracellular matrix, have been chosen. Therefore, the three-dimensional structure of said polypeptides was obtained.

Consequently, synthetic molecules belonging to the same family were designed, containing a motif similar to the RGD of the template, having potential biological activity but lacking of peptide bonds in order to be less sensible to proteolitic degradation in vivo.

After said design step, the more interesting molecule of the family, i.e. the easiest to be produced and the one showing highest similarity to the template, was synthesised and tested in vitro.

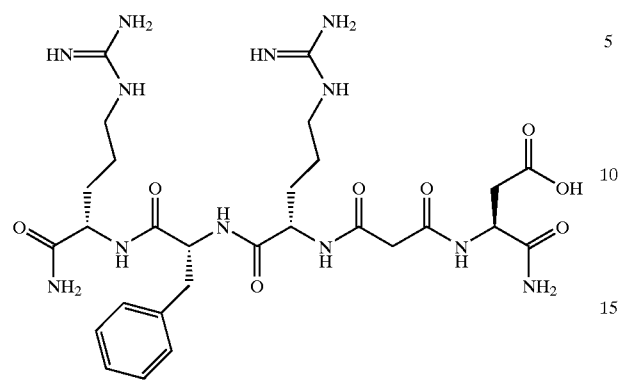

Said RGD-analog molecule with no intramolecular peptidic bonds, was tested in smooth muscle rat cells, and showed the capability to strongly inhibit cellular adhesion to extra-cellular matrix and to inhibit PDGF-induced (platelet derived grow factor) cellular migration and proliferation.

These data indicate that this new molecule might be used as inhibitor of abnormal migration and proliferation of vascular cells that occur in several vascular diseases such as atherosclerosis and restenosis, as well as of migration of neoplastic cells toward the potential metastatic sites.

Designing RGD-peptidomimetics

According to the previous observations, RGD-containing peptides were chosen as templates to design peptidomimetic molecules.

This choice was made considering carefully the reports on the biological activity of RGD-containing peptides available in literature and using useful and specific databases for the identification of known structural conformations (PDB databases).

Once the three-dimensional conformation of the RGD motif in the template peptide to be used in the simulation was identified, the designing process of similar molecules was performed and molecules belonging to the same family and showing the same features were obtained.

The molecules belonging to the same family are showed as follows:

Mimic-polypeptide 1: (H$_2$N—RmRmD—NH$_2$)

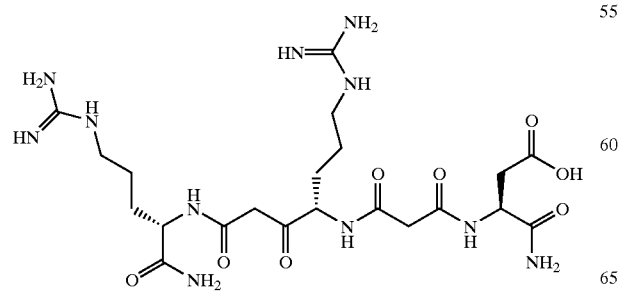

Mimic-polypeptide 2: (H$_2$N—RphacRmD—NH$_2$)

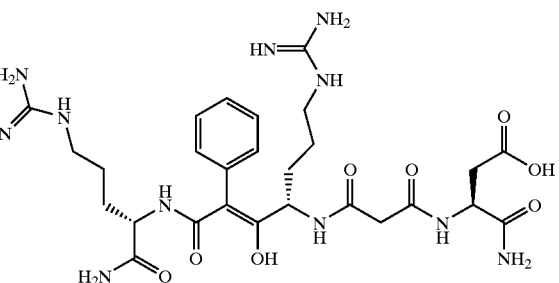

Mimic-polypeptide 3 (H$_2$N—RvRmD—NH$_2$)

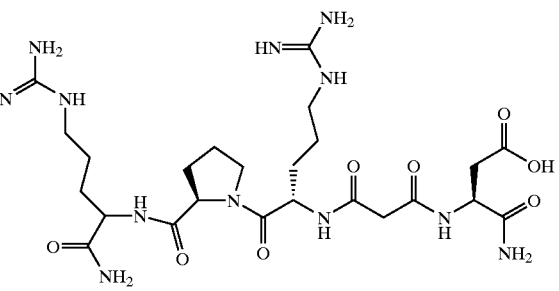

Mimic-polypeptide 4 (H$_2$N—RpRmD—NH$_2$):

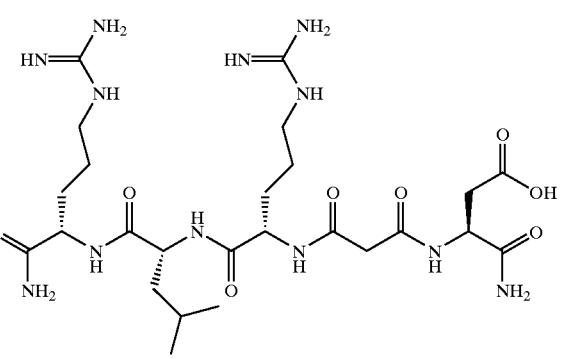

Mimic-polypeptide 5 (H$_2$N—RlRmD—NH$_2$)

Mimic-polypeptide 6 (H₂N—RfRmD—NH₂):

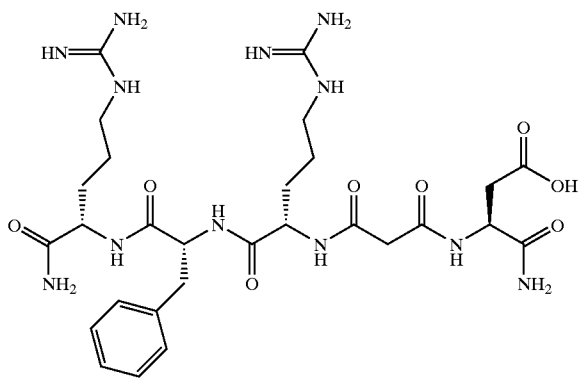

Mimic-polypeptide 7 (H₂N—RnleuRmD—NH₂)

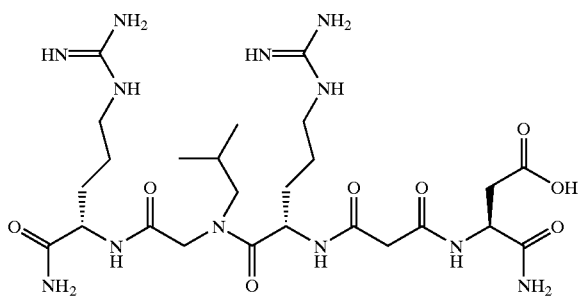

Mimic-polypeptide 8 (H₂N—R1RmD—NH₂)

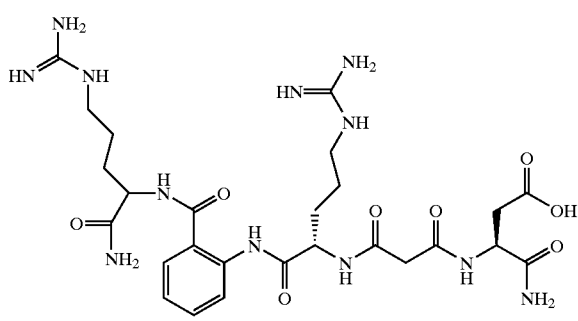

Between all the molecules belonging to the same family, molecule nr. 6 was synthesized and hereafter named as non-peptidic RGD-analog molecule.

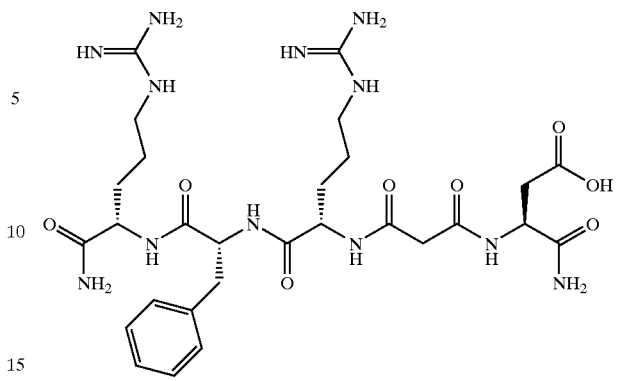

In vitro experiments were performed on said molecule confirming the functional characteristics of the molecule family.

RGD-analogs Activity in vitro Testing

For this test rat vascular smooth muscle cells (RASMC) primary cultures, obtained from adult male Wistar Rats, were used according to well known procedures (Facchiano et al., 2000, J. Cell Sci., 113(16), 2855–63).

Adhesion Assay

Adhesion assay was carried out on 96 well plates, activated with 50 microliters of a solution containing Vitronectin (20 microliters/milliliter). Saturation of aspecific sites was obtained incubating with bovine serum albumin (BSA) (5 mg/ml in Dulbecco-modified eagle's medium, DMEM) for 1 hour at 37° C. Then, wells were washed once with DMEM and 30.000 cells/well were dispensed in the presence or absence of the molecule to be tested. After an incubation of 1 hour at 37° C., to allow cells adhesion to the vitronectin matrix, wells were washed twice with PBS and cells were fixed with formaldehyde 4% in PBS, for 10 minutes at room temperature. After a further washing with PBS, cells were stained with Toluidine Blue (0.5% in formaldehyde 4%) for 10 minutes at room temperature. The stain absorbed within the cells was extracted with SDS 1% for 30 minutes, and quantified with an ELISA rider at a wavelength of 595 nanometers.

Migration Assay

Migration assay was carried out in modified Boyden chambers (Costar Scientific Corporation) following a well known standard procedure (Facchiano, et al., 2000, J. Cell Sci., 113(16),2855–63). Rat vascular smooth muscle cells (RASMC) were placed in the upper chamber of the Boyden apparatus. The used chemoattractant was human recombinant platelet derived growth factor (PDGF-BB) (R & D Systems), which is the most potent chemoattractant described for vascular smooth muscle cells (VSMC); it was dissolved at 10 ng/ml in DMEM-0,1% BSA and placed in the lower chamber of the Boyden apparatus. Cell migrated on the bottom face of the filters were counted at 400× magnification. Fifteen fields were counted for each filter and the average number of cells/field was calculated. Experiments were performed at least 4 times in duplicate. The experimental results show the different migration capacity of tested molecules in comparison with no-treated cells.

Proliferation Assay

Proliferation assay was performed, following standard procedures (Facchiano, et al., 2000, Cell Sci., 113(16), 2855–63), on 6-well plates ($1 \times 10^5$ cells/plate) allowed to grow for 24 hours in DMEM supplemented with 10% Fetal Calf Serum (FCS) at 37° C. in 5% $CO_2$. Medium was replaced with starvation medium containing either DMEM-0.1% BSA for 24 hours. Subsequently the starvation medium was replaced with fresh medium containing either 0.1% BSA alone or 0.1% BSA with PDGF-BB in the presence or absence of the RGD-analog. Every assay was carried out at different time intervals and cells were harvested and counted with hemacytometer.

The results of the three assays are shown in FIGS. 1, 2 and 3 as follows:

FIG. 1 compares dose-dependent inhibition of RASMC adhesion to vitronectin, induced by RGDS (used as positive control with known activity) and non-peptidic RGD-analog;

FIG. 2 compares dose-dependent inhibition of RASMC migration toward PDGF-BB gradient, induced by RGDS and non-peptidic RGD-analog;

FIG. 3 compares dose-dependent inhibition of RASMC proliferation stimulated for 48 hours with PDGF-BB (10 ng/ml) induced by RGDS and non-peptidic RGD-analog (100 ng/ml).

The results indicate that RGD-analog inhibits RASMC adhesion to vitronectin (FIG. 1) and RASMC migration toward PDGF-BB (FIG. 2) in a dose-dependent manner and in a fashion quite similar to the template molecule (RGDS peptide, used as positive control in these experiments).

Proliferation experiments show a marked anti-proliferative effect of the non-peptidic RGD-analog, at 100 nanogramms/ml concentration, as well as of the positive control RGDS. Both molecules do not show toxic effects if added to cells in the absence of PDGF-BB (FIG. 3).

The results collected indicate:
1. the novel synthesised molecule and all the other non-peptidic RGD-analogs as described, mimic perfectly the activity of the template RGDS, indicating that the aim of constructing a family of molecules able to mimic RGD-peptide was achieved.
2. The novel synthesised molecule and all the other non-peptidic RGD-analogs as described, did not show, in the assay performed, any aspecific citotoxic effect.
3. The novel synthesised molecule and all the other non-peptidic RGD-analogs as described, strongly inhibit adhesion, migration and proliferation of RASMC, indicating that these molecules are good candidates for further in vivo investigation. In fact, said molecules, thanks to their chemical characteristics, are expected to act in vivo better than the template RGDS.

RGDS is known to have a strong biological activity in vivo: it is evident that non-peptidic RGD-analogs might be used for the treatment of vascular diseases, as inhibitors of primary tumour growth and metastasis. Therefore, the use of said molecules dispersed in a solution or immobilised on synthetic and/or biological matrix can be assumed. In particular, in the first case, these molecules can inhibit cellular adhesion, migration and proliferation. In the second case, these molecules can stimulate cellular adhesion. Consequently, said molecules might enhance biocompatibility of synthetic and/or biological materials that are used in transplant and/or graft and more particularly in the case of vessels or cardiac valves grafts due to ischemic or cardiovascular diseases.

What is claimed is:

1. Non-peptidic RGD-analog molecule having the following structure:

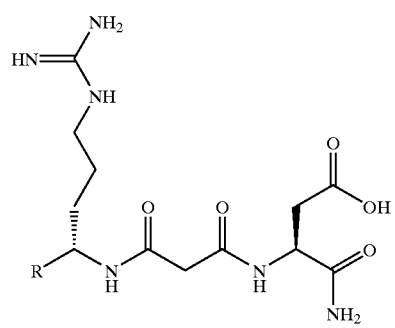

wherein R is selected between the following structures:

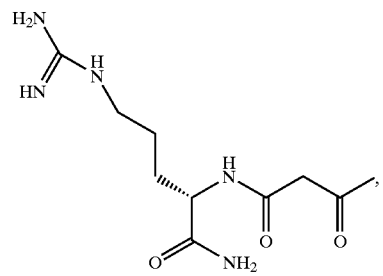

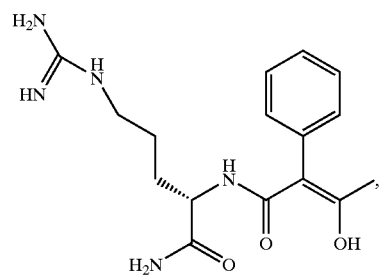

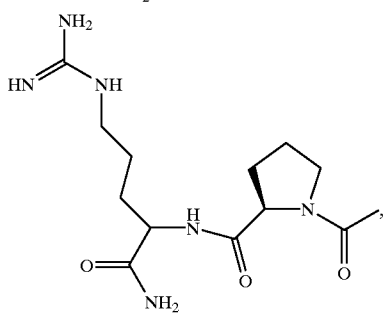

-continued

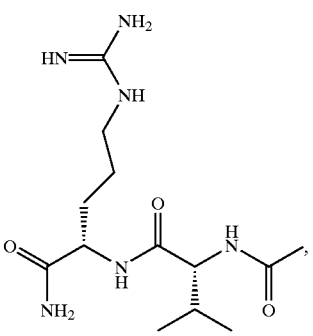

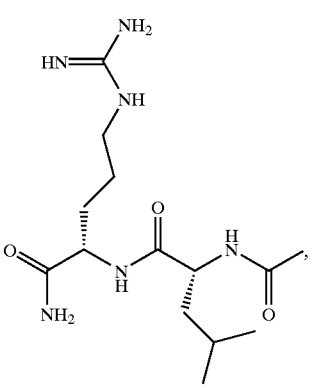

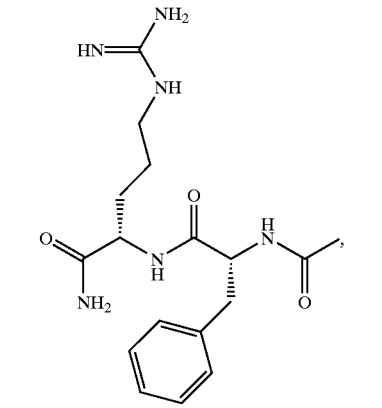

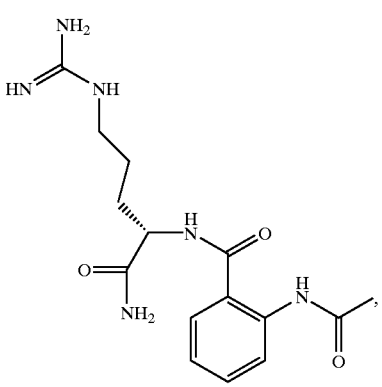

-continued

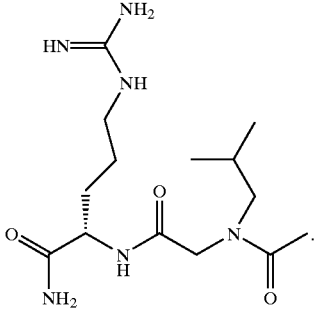

2. Non-peptidic RGD-analog molecule having the following structure:

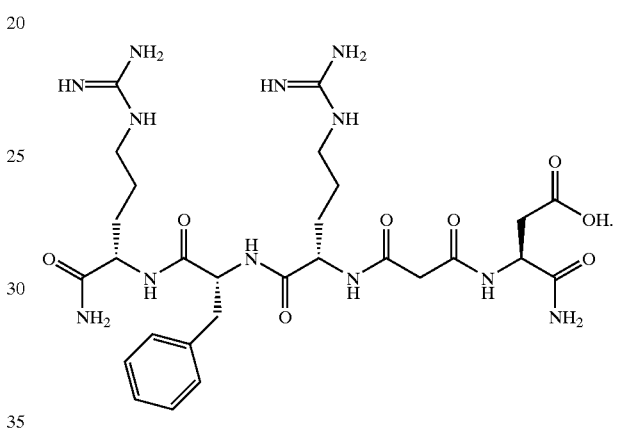

3. A method for treating vascular diseases in a patient, comprising:
   administering to said patient an effective amount of the non-peptidic molecule according to claim 1.

4. A method for inhibiting primary tumor growth and metastasis in a patient, comprising:
   administering to said patient an effective amount of the non-peptidic molecule according to claim 1.

5. A method for inhibiting integrin-mediated diseases in a patient, comprising:
   administering to said patient an effective amount of the non-peptidic molecule according to claim 1.

6. A method for inhibiting cellular proliferation and migration of neoplastic cells toward metastatic sites in a patient, comprising:
   administering to said patient an effective amount of the non-peptidic molecule according to claim 1.

7. A method for the treatment of neoplastic and vascular diseases in a patient, comprising:
   administering to said patient an effective amount of the non-peptidic molecule according to claim 1.

8. A method for the treatment of RGD-protein-mediated diseases in a patient, comprising:
   administering to said patient an effective amount of the non-peptidic molecule according to claim 1.

9. A method for the treatment of diseases related to RGD-motif binding activity in a patient, comprising:

administering to said patient an effective amount of the non-peptidic molecule according to claim 1.

10. A method for enhancing biocompatibility and therapeutic efficacy of a synthetic and/or biological matrix in a patient, administering to said patient an effective amount of the non-peptidic molecule according to claim 1.

11. A method for modulating an immunological response in a patient, comprising:

administering to said patient an effective amount of the non-peptidic molecule according to claim 1.

12. A method for treating thrombotic events in a patient, comprising:

administering to said patient an effective amount of the non-peptidic molecule according to claim 1.

13. A method for inducing apoptosis in a patient, comprising:

administering to said patient an effective amount of the non-peptidic molecule according to claim 1.

14. A method for treating vascular diseases in a patient, comprising:

administering to said patient an effective amount of the non-peptidic molecule according to claim 2.

15. A method for inhibiting primary tumor growth and metastasis in a patient, comprising:

administering to said patient an effective amount of the non-peptidic molecule according to claim 2.

16. A method for inhibiting integrin-mediated diseases in a patient, comprising:

administering to said patient an effective amount of the non-peptidic molecule according to claim 2.

17. A method for inhibiting cellular proliferation and migration of neoplastic cells toward metastitic sites in a patient, comprising:

administering to said patient an effective amount of the non-peptidic molecule according to claim 2.

18. A method for the treatment of neoplastic and vascular diseases in a patient, comprising:

administering to said patient an effective amount of the non-peptidic molecule according to claim 2.

19. A method for the treatment of RGD-protein-mediated diseases in a patient, comprising:

administering to said patient an effective amount of the non-peptidic molecule according to claim 2.

20. A method for the treatment of diseases related to RGD-motif binding activity in a patient, comprising:

administering to said patient an effective amount of the non-peptidic molecule according to claim 2.

21. A method for enhancing biocompatibility and therapeutic efficacy of a synthetic and/or biological matrix in a patient, comprising:

administering to said patient effective amount of the non-peptidic molecule according to claim 2.

22. A method for modulating an immunological response in a patient, comprising:

administering to said patient an effective amount of the non-peptidic molecule according to claim 2.

23. A method for treating thrombotic events in a patient, comprising:

administering to said patient an effective amount of the non-peptidic molecule according to claim 2.

24. A method for inducing apoptosis in a patient, comprising:

administering to said patient an effective amount of the non-peptidic molecule according to claim 2.

* * * * *

UNITED STATES PATENT AND TRADEMARK OFFICE
CERTIFICATE OF CORRECTION

PATENT NO. : 6,627,769 B2
DATED : September 30, 2003
INVENTOR(S) : Antonio Facchiano et al.

It is certified that error appears in the above-identified patent and that said Letters Patent is hereby corrected as shown below:

<u>Title page,</u>
Item [73], Assignee, change "Congregzaione" to -- Congregazione --.

Signed and Sealed this

Thirtieth Day of December, 2003

JAMES E. ROGAN
*Director of the United States Patent and Trademark Office*